United States Patent
Reschke et al.

(10) Patent No.: US 9,017,370 B2
(45) Date of Patent: Apr. 28, 2015

(54) VESSEL SEALER AND DIVIDER WITH CAPTURED CUTTING ELEMENT

(75) Inventors: Arlan J. Reschke, Longmont, CO (US); Jeffrey M. Roy, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1107 days.

(21) Appl. No.: 13/029,481

(22) Filed: Feb. 17, 2011

(65) Prior Publication Data

US 2012/0215215 A1 Aug. 23, 2012

(51) Int. Cl.
*A61B 18/14* (2006.01)
*A61B 18/00* (2006.01)

(52) U.S. Cl.
CPC ......... *A61B 18/1445* (2013.01); *A61B 18/1442* (2013.01); *A61B 2018/0063* (2013.01); *A61B 2018/1455* (2013.01)

(58) Field of Classification Search
USPC ...................................... 606/45–52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,389,098 A * | 2/1995 | Tsuruta et al. ................. 606/41 |
| D358,887 S | 5/1995 | Feinberg |
| 5,611,808 A | 3/1997 | Hossain et al. |
| D384,413 S | 9/1997 | Zlock et al. |
| 5,797,938 A | 8/1998 | Paraschac et al. |
| D402,028 S | 12/1998 | Grimm et al. |
| 5,960,544 A | 10/1999 | Beyers |
| D416,089 S | 11/1999 | Barton et al. |
| D424,694 S | 5/2000 | Tetzlaff et al. |
| D425,201 S | 5/2000 | Tetzlaff et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler.

(Continued)

*Primary Examiner* — Michael Peffley

(57) ABSTRACT

The present disclosure relates to an end effector assembly including first and second jaw members and a knife body. The first and second jaw members have a curved configuration and are disposed in opposed relation to each other. One or both of the jaw members include a ledge, a first knife channel and a second knife channel. The ledge is disposed along the length of one of the jaw members. The first knife channel is defined along the length of a portion of the ledge. The second knife channel is defined along the length of a portion of the jaw member, and below a bottom portion of the ledge such that the ledge covers a portion of the second knife channel. The knife body includes a knife blade at a distal end thereof and a recessed portion proximal to the knife blade.

19 Claims, 7 Drawing Sheets

(56) References Cited

U.S. PATENT DOCUMENTS

| | | | |
|---|---|---|---|
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| 6,482,205 B1 | 11/2002 | Bonnet | |
| D493,888 S | 8/2004 | Reschke | |
| 6,790,217 B2 * | 9/2004 | Schulze et al. | 606/171 |
| D496,997 S | 10/2004 | Dycus et al. | |
| D499,181 S | 11/2004 | Dycus et al. | |
| D502,994 S | 3/2005 | Blake, III | |
| 6,905,497 B2 * | 6/2005 | Truckai et al. | 606/49 |
| D509,297 S | 9/2005 | Wells | |
| D525,361 S | 7/2006 | Hushka | |
| 7,101,373 B2 | 9/2006 | Dycus et al. | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,766,910 B2 | 8/2010 | Hixson et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2002/0099371 A1 | 7/2002 | Schulze | |
| 2003/0055424 A1 | 3/2003 | Ciarrocca | |
| 2005/0096651 A1 * | 5/2005 | Truckai et al. | 606/51 |
| 2006/0189981 A1 | 8/2006 | Dycus et al. | |
| 2008/0021450 A1 | 1/2008 | Couture | |
| 2009/0012520 A1 | 1/2009 | Hixon et al. | |
| 2010/0274244 A1 * | 10/2010 | Heard | 606/45 |
| 2011/0009864 A1 | 1/2011 | Bucciaglia | |
| 2011/0060334 A1 | 3/2011 | Brandt et al. | |
| 2011/0087221 A1 * | 4/2011 | Siebrecht et al. | 606/45 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 92/06642 | 4/1992 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/576,380, filed Oct. 9, 2009, Wayne Siebrecht.
U.S. Appl. No. 12/607,191, filed Oct. 28, 2009, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.

(56) References Cited

OTHER PUBLICATIONS

U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.

(56) References Cited

OTHER PUBLICATIONS

Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Intl Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Intl Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 12155726.8 dated May 14, 2012.

\* cited by examiner

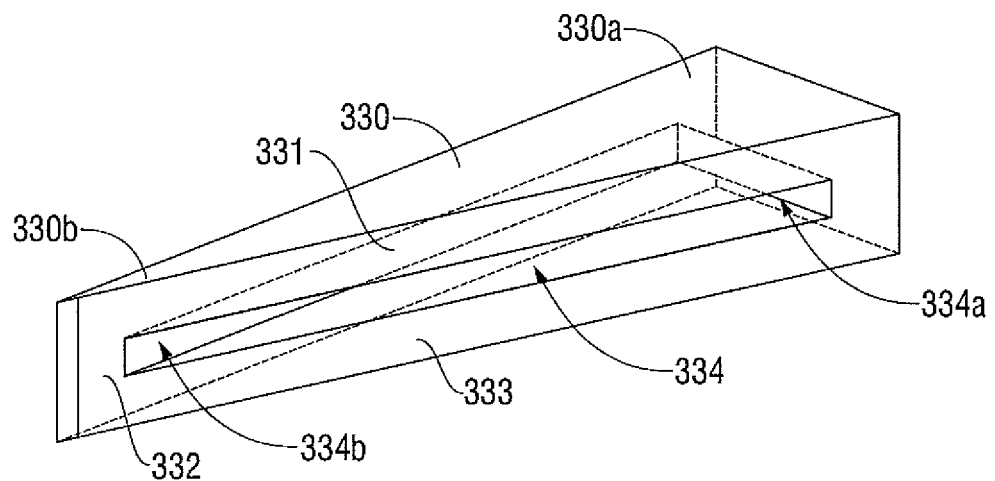
FIG. 10
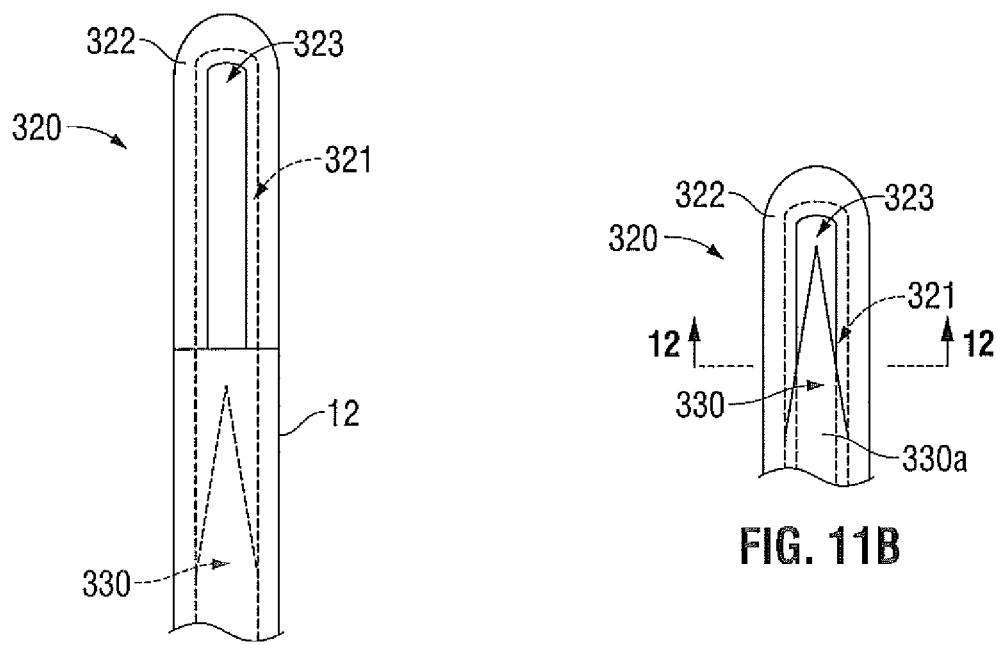
FIG. 11A
FIG. 11B

VESSEL SEALER AND DIVIDER WITH CAPTURED CUTTING ELEMENT

BACKGROUND

1. Technical Field

The present disclosure relates to surgical instruments. More particularly, the present disclosure relates to surgical instruments having sealing and cutting capabilities.

2. Description of Related Art

During a typical surgical procedure, for example, an open or endoscopic electrosurgical procedure, a clinician may, in certain circumstances, have to remove an electrosurgical instrument from an operative site, substitute a new instrument, and accurately sever a vessel, which was previously electrosurgically treated. As can be appreciated, this additional step may be both time consuming (particularly when treating multiple operative sites) and may contribute to imprecise separation of the tissue due to the misalignment or misplacement of the severing instrument along the previously electrosurgically treated tissue.

Many surgical instruments have been designed which incorporate a knife blade or blade member that effectively severs the tissue after an electrosurgical procedure has been performed. For example, commonly-owned U.S. Pat. Nos. 7,083,618 and 7,101,371 describe one such electrosurgical instrument that effectively seals and cuts tissue along the formed tissue seal. Other instruments include blade members or shearing members which simply cut tissue in a mechanical and/or electromechanical manner and are relatively ineffective for electrosurgical procedures.

In some instances, during a cutting procedure, the knife blade tends to dislodge from the knife channel or intended knife path (e.g., bow upwards) during actuation, which may cause the knife blade to lock up and inefficiently cut tissue. In other instances, during a cutting stroke, the knife blade member may frictionally drag alongside the knife channel, giving a user a false sense that a cut was successfully performed.

SUMMARY

The present disclosure relates to an end effector assembly including first and second jaw members and a knife body. The first and second jaw members have a curved configuration and are disposed in opposed relation to each other. One or both of the jaw members are moveable from a first, open position to a second, closed position for grasping tissue therebetween. One or both of the first and second jaw members includes an electrically conductive sealing surface. One or both of the jaw members include a ledge, a first knife channel and a second knife channel. The ledge is disposed along the length of one of the jaw members. The ledge includes a top portion and a bottom portion. The first knife channel is defined along the length of a portion of the ledge. The second knife channel is defined along the length of a portion of the jaw member, and below the bottom portion of the ledge such that the ledge covers a portion of the second knife channel. The knife body includes a knife blade at a distal end thereof and a recessed portion proximal to the knife blade. In this configuration, the knife blade travels within the first knife channel and the recessed portion travels within the second knife channel.

In embodiments, each of the jaw members includes an electrode plate for sealing tissue, and includes another ledge. The knife blade may be configured to cam along the first knife channel and the recessed portion may be configured to earn along the second knife channel under a bottom portion of the ledge.

In embodiments, the knife body is translated along an apex of the curved jaw members such that the knife body flexes to maintain a radius to reduce friction along the wall of the knife channel. A sharp cutting edge may be defined on proximal and distal portions of the knife blade such that when the knife blade is translated in a distal direction, the distal portion of knife blade cuts tissue a first time, and when the knife blade is translated proximal direction, the proximal portion of the knife blade cuts tissue a second time.

The bottom portion of the ledge may be configured to capture the recessed portion of the knife body to prevent the knife body from dislodging in an upward, distal direction and out of the first knife channel.

In embodiments, the top portions of the electrode plates oppose each other and are configured to contact and grasp tissue when the jaw members are approximated towards each other in the closed position.

The present disclosure also relates to an end effector assembly including first and second jaw members and a knife body. The first and second jaw members have a curved configuration and are disposed in opposed relation to each other. One or both of the jaw members are moveable from a first, open position to a second, closed position for grasping tissue therebetween. Further, one or both of the jaw members may include an electrode plate, a first knife channel and a second knife channel. The electrode plate for sealing tissue includes a top portion and a bottom portion. The first knife channel defined along the length of a portion of the electrode plate. The second knife channel defined along the length of a portion of the jaw member below the bottom portion of the electrode plate. The knife body includes a knife blade at a distal end thereof and a slot defined therein. The slot is configured to span along at least a portion of a length of the knife body. The knife body includes a top portion that is disposed above the slot, and a bottom portion that is disposed below the slot. In this configuration, the knife blade is configured to cam along at least one of the first knife channels and the slot is configured to receive the electrode plate.

In embodiments, the knife body is translated along an apex of the curved jaw members such that the knife body flexes to maintain a radius to reduce friction along the wall of the knife channel. The top portion of the knife body may be configured to cam below the bottom portion of the electrode plate of the first jaw member, and the bottom portion of the knife body may be configured to cam below the bottom portion of the electrode plate of the second jaw member.

In embodiments, the slot is configured to capture a portion of the electrode plate and the bottom portion of the electrode plate cams along one or both of the top and bottom portions of the knife body. The slot may be configured to capture the bottom surface of the electrode plate to prevent knife splay and maintains the jaw members in the second, closed position.

In embodiments, the knife blade is translated in a distal direction through the second knife channel to thereby cut tissue disposed between the jaw members.

The present disclosure further relates to an end effector assembly including first and second jaw members and a knife body. The first and second jaw members are disposed in opposed relation to each other. One or both of the jaw members are moveable from a first, open position to a second, closed position for grasping tissue therebetween. One or both of the jaw members may include an electrode plate and first and second knife channels. The electrode plate for sealing tissue includes a top portion and a bottom portion. The first knife channel is defined along the length of a portion of the electrode plate and the second knife channel is defined along the length of a portion of the jaw member below the bottom portion of the electrode plate. Further, the knife body includes a knife blade at a distal end thereof and a slot defined therein. The slot is configured to span along at least a portion of a length of the knife body. The knife body includes a top portion that is disposed above the slot, and a bottom portion that is disposed below the slot. In this configuration, the knife body includes a proximal portion and a distal portion, the knife body having a tapered configuration such that a width of the proximal portion is larger than a width of the distal portion.

In embodiments, the proximal portion of the slot cams the bottom portion of the electrode plate, as the knife body is translated in a distal direction, and maintains the first and second jaw members in the second, closed position.

In embodiments, the slot of the knife body includes a distal portion that tapers towards a proximal portion such that as the knife body is translated in a distal direction the slot exerts pressure towards inner edges of the electrode plates.

BRIEF DESCRIPTION OF THE DRAWINGS

The above and other aspects, features, and advantages of the present disclosure will become more apparent in light of the following detailed description when taken in conjunction with the accompanying drawings in which:

FIG. 10 is a side, perspective view of a knife body of an end effector assembly, according to an embodiment of the present disclosure;

FIGS. 11A and 11B are top, plan views of a jaw member showing the knife body of FIG. 10 in an unactuated position and an actuated position, respectively;

DETAILED DESCRIPTION

Figure 1A:
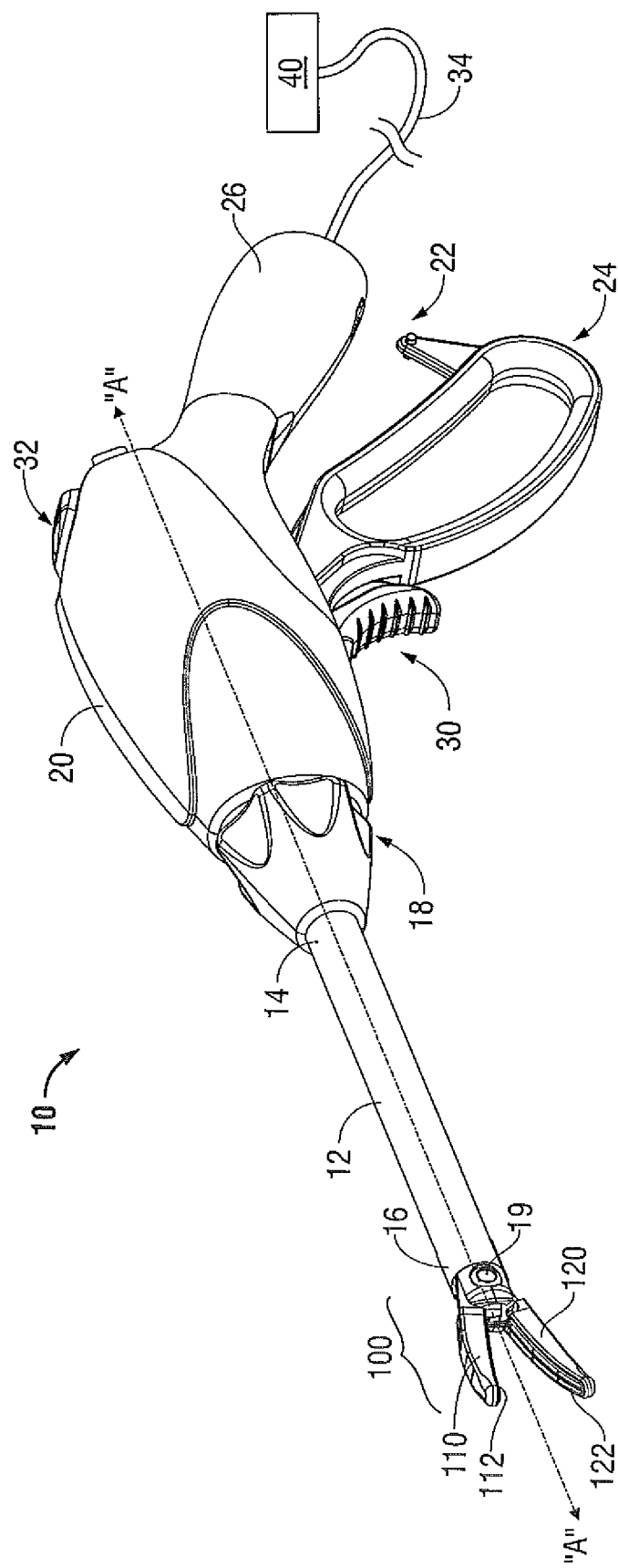
FIG. 1A is a perspective view of the endoscopic forceps including an end effector assembly of FIG. 2, according to an embodiment of the present disclosure.

Embodiments of the presently disclosed electrosurgical instrument are described in detail with reference to the drawings wherein like reference numerals identify similar or identical elements. As used herein, the term "distal" refers to that portion which is further from a user while the term "proximal" refers to that portion which is closer to a user.

In general, the present disclosure relates to a cutting assembly that is configured to capture and retain a knife body within a knife channel of a jaw member during translation thereof. In embodiments, the knife body includes a recessed portion and a blade portion. In this configuration, the recessed portion of the knife body is captured and retained within the knife channel and below an electrode plate of an electrode, while the blade portion of the knife body travels within the knife channel and above the electrode plate to cut tissue grasped between jaw members.

In other embodiments, the knife body includes an elongated slot that is configured to capture the inner peripheral edges of the top and bottom electrode plates. In this configuration, as the knife body travels along the knife channel (e.g., in a curved jaw member) during tissue division, the elongated slot captures the edges of the top and bottom electrode plates to prevent the jaw members from separating (e.g., opening). The aforementioned embodiments and other embodiments are described in greater detail below.

Figure 1B:
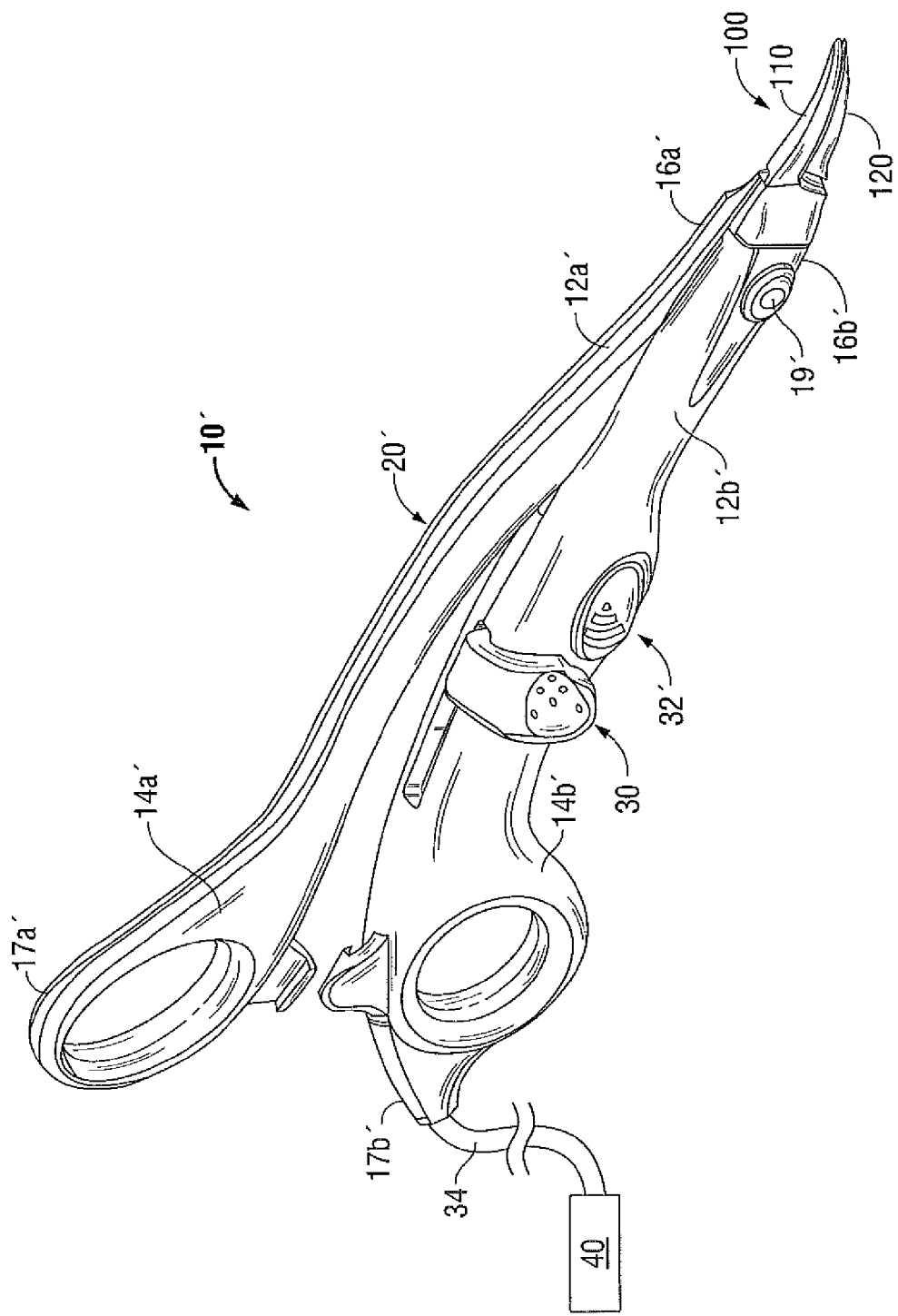
FIG. 1B is a perspective view of the open forceps including an end effector assembly of FIG. 2, according to an embodiment of the present disclosure.

Referring now to the figures, FIG. 1A depicts an endoscopic forceps 10 as used in correlation with endoscopic surgical procedures and FIG. 1B depicts an open forceps 10' as used in correlation with open surgical procedures. For the purposes herein, either an endoscopic instrument or an open surgical instrument may be utilized with the novel cutting assembly described herein. It should be noted that different electrical and mechanical connections and other considerations may apply to each particular type of instrument. However, the novel aspects with respect to the cutting assembly described herein and the operating characteristics thereof remain generally consistent with respect to both the endoscopic or open surgical designs.

The forceps 10 is coupled to an electrosurgical energy source and is configured to seal tissue using radiofrequency (RF) energy. The electrosurgical energy source (e.g., generator 40) is configured to output various types of energy, such as RF energy having any suitable frequency. Forceps 10 is coupled to generator 40 via a cable 34 that is adapted to transmit the appropriate energy and control signals therebetween.

Forceps 10 is configured to support an end effector assembly 100 and typically includes various conventional features (e.g., a housing 20, a handle assembly 22, a rotating assembly 18, and a trigger assembly 30) that enable a pair of jaw members 110 and 120 to mutually cooperate to grasp, seal and divide tissue. Handle assembly 22 includes a moveable handle 24 and a fixed handle 26 that is integral with housing 20. Handle 24 is moveable relative to fixed handle 26 to actuate the jaw members 110 and 120 via a drive assembly (not explicitly shown) to grasp and treat tissue. Forceps 10 also includes a shaft 12 having a distal portion 16 that mechanically engages end effector assembly 100 and a proximal portion 14 that mechanically engages housing 20 proximate rotating assembly 18 disposed on housing 20. Rotating assembly 18 is mechanically associated with shaft 12 such that rotational movement of rotating assembly 18 imparts similar rotational movement to shaft 12 which, in turn, rotates end effector assembly 100.

End effector assembly 100 includes jaw members 110 and 120 each having an electrode 112 and 122, respectively, associated therewith and on an inner facing surface thereof. One or both of the jaw members 110 and 120 are pivotable about a pivot pin 19 and are movable from a first position wherein the jaw members 110 and 120 are spaced relative to another, to a second position wherein the jaw members 110 and 120 are closed and cooperate to grasp tissue therebetween. As discussed in more detail below, end effector assembly 100 is adapted for use with an RF energy source.

More particularly, electrodes 112 and 122 are connected to generator 40 and configured to communicate electrosurgical energy through tissue held therebetween. Electrodes 112 and 122 cooperate to grasp, coagulate, seal, cut, and/or sense tissue held therebetween upon application of energy from generator 40.

Figure 2:
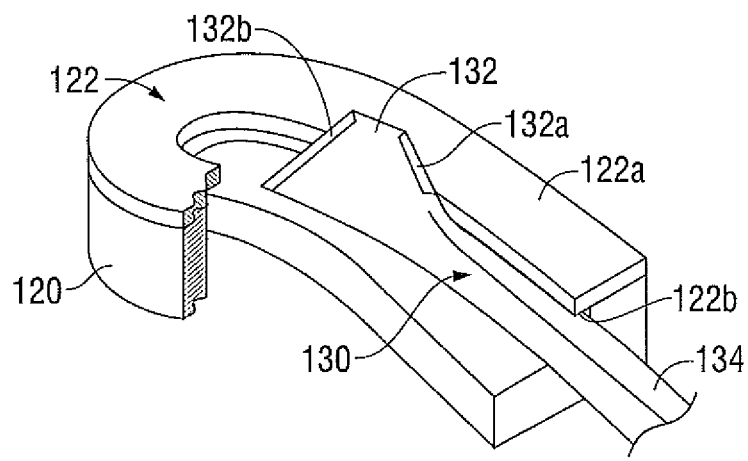
FIG. 2 is a rear, cut-out, perspective view of a jaw member of an end effector assembly showing a knife body actuated therethrough, according to an embodiment of the present disclosure.
Figure 3:
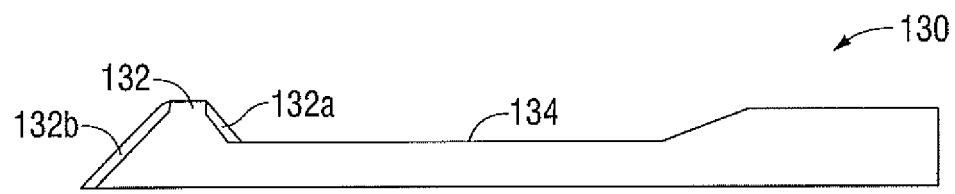
FIG. 3 is a side, elevational view of the knife body of FIG. 2.
Figure 4:
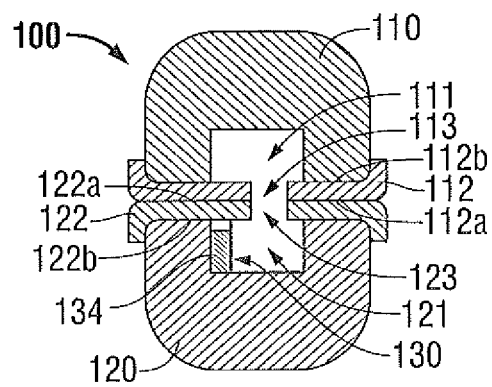
FIG. 4 is a front, cross-sectional view of the end effector assembly of FIG. 2.

Trigger assembly 30 is configured to actuate a knife body (as shown in FIGS. 2-4) disposed within forceps 10 and between the jaw members 110 and 120 to selectively sever tissue that is grasped between jaw members 110 and 120. Switch assembly 32 is configured to allow a user to selectively provide electrosurgical energy to end effector assembly 100. A cable 34 connects the forceps 10 to generator 40 to provide electrosurgical energy (e.g., RF energy) to the jaw members 110 and 120 through various conductive paths and ultimately to end effector assembly 100.

Referring now to FIG. 1B, an open forceps 10' is depicted and includes end effector assembly 100 (similar to forceps 10) that is attached to a handle assembly 20' having a pair of elongated shaft portions 12a' and 12b'. Each elongated shaft portion 12a' and 12b' has a proximal end 14a' and 14b', respectively, and a distal end 16a' and 16b', respectively. Similar to forceps 10, end effector assembly 100 includes jaw members 110 and 120 that attach to distal ends 16a' and 16b' of shafts 12a' and 12b', respectively. Jaw members 110 and 120 are connected about a pivot pin 19' to allow jaw members 110 and 120 to pivot relative to one another from the first to second positions for treating tissue (as described above).

Each shaft 12a' and 12b' includes a handle 17a' and 17b', respectively, disposed at the proximal end 14a' and 14b' thereof. Handles 17a' and 17b' facilitate movement of the shafts 12a' and 12b' relative to one another which, in turn, pivot the jaw members 110 and 120 from an open position such that the jaw members 110 and 120 are disposed in spaced relation relative to one another to a clamped or closed position such that the jaw members 110 and 120 cooperate to grasp tissue therebetween.

Forceps 10' includes a trigger assembly 30' (similar to forceps 10) that is configured to actuate a knife body 130 (as shown in FIG. 2-4) disposed within shaft 12b'. The knife body 130 is configured to allow a user to selectively sever tissue that is grasped between jaw members 110 and 120. One or more of the shafts, e.g., shaft 12a', includes a switch assembly 32' (similar to forceps 10) that is configured to allow a user to selectively provide electrical energy to the end effector assembly 100. In a similar fashion to forceps 10, cable 34 of forceps 10' is internally divided within the shaft 12b' to transmit electrosurgical energy through various conductive pathways to the components of end effector assembly 100.

Referring now to FIGS. 2-4, end effector assembly 100 includes a pair of opposing jaw members 110, 120 each defining a knife channel 111, 121, respectively therein. Knife channels 111 and 121 are configured to allow a knife body 130 to pass therethrough when knife body 130 is selectively actuated by a user in order to sever tissue grasped between jaw members 110 and 120. Jaw members 110 and 120 each include respective electrode plates 112 and 122 that are disposed atop the jaw members 110 and 120. Each electrode plate 112, 122 includes a top portion (e.g., tissue contacting surface) 112a, 122a, respectively, and a bottom portion 112b, 122b, respectively.

Top portions 112a and 122a of electrode plates 112 and 122 oppose each other, and are configured to contact and grasp tissue when jaw members 110 and 120 are approximated towards each other in a closed position. Top portions 112a and 122a also provide for a tissue treating surface area for treating tissue (e.g., sealing and coagulation).

Each electrode plate 112, 122 defines a respective knife channel 113, 123 to allow access for a knife blade 132 of knife body 130 to pass therethrough. A portion of electrode plate 112, 122 forms a ledge over knife channel 111, 121, respectively. In this configuration, a part of bottom portion 112b, 122b (e.g., the ledge) is over knife channel 111, 121 such that a portion of electrode plate 112, 122 (e.g., the ledge) covers knife channel 111, 121.

Figure 5:
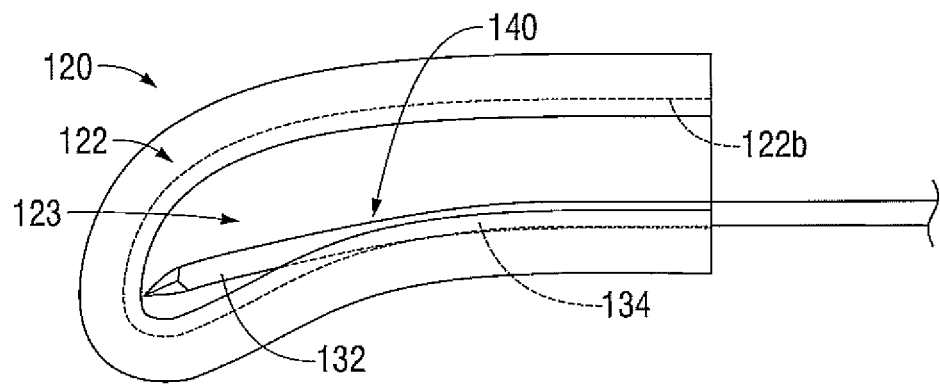
FIG. 5 is a top, plan view of the jaw member of FIG. 2 showing the knife body actuated therethrough, according to an embodiment of the present disclosure.

Knife channels 111 and 121 and knife channels 113 and 123 are configured to span along the jaw members 110 and 120 in either a straight configuration (e.g., along a longitudinal axis) or a curved configuration when jaw members 110 and 120 have a curved jaw configuration, as shown in FIGS. 2, 4 and 5.

In some embodiments, electrode plates 112 and 122 may be attached to the jaw member 110, 120 by stamping, by overmolding, by casting, by overmolding a casting, by coating a casting, by overmolding a stamped electrically conductive sealing plate and/or by overmolding a metal injection molded seal plate or in other ways customary in the art. All of these manufacturing techniques may be employed to produce jaw member 110 and 120 having an electrically conductive electrode plates 112 and 122 disposed thereon for contacting and treating tissue.

As discussed above, knife body 130 includes a knife blade 132 that is positioned on a distal end of knife body 130. A sharp cutting edge may be defined on both proximal and distal portions, 132a and 132b, of knife blade 132. In this manner, when the knife blade 132 is translated or reciprocated in a distal direction, distal portion 132b of knife blade 132 cuts and divides tissue that is grasped between jaw members 110 and 120. Additionally, when the knife blade 132 is translated or reciprocated in a returning proximal direction, proximal portion 132a of knife blade 132 cuts and divides tissue a second time in a proximal direction. Knife body 130 also includes a recessed portion 134 that is tapered downwardly (e.g., a height less than the height of knife channel 121) such that recessed portion 134 is captured and retained underneath a bottom portion 122b of electrode plate 122.

During use, when jaw members 110 and 120 are in the closed, second position and have grasped tissue therebetween, knife trigger assembly 30 is actuated by a user to cause knife body 130 to translate in a distal direction along jaw members 110 and 120. Accordingly, recessed portion 134 translates through knife channel 121 while knife blade 132 translates through knife channels 111, 113, and 123 to thereby cut tissue disposed between jaw members 110 and 120 (e.g., along a tissue seal). Typically, when a curved jaw member configuration is utilized, recessed portion 134 is captured within knife channel 121 and underneath bottom portion 122b of electrode plate 122, since recessed portion 134 has a lower profile (e.g., reduced height) than knife channel 121. In this configuration, only recessed portion 134 is contained within knife channel 121 where it is captured and/or guided, thus reducing knife splay and allows knife body 130 to travel in a guided, designated path. Further, recessed portion 134 allows knife body 130 to maintain symmetrical strength while cutting tissue and provides structural support in order to maintain cutting forces focused in the cutting direction.

In other embodiments and as depicted in FIG. 5, depending on the manufacturing and material of knife body 130, knife body 130 may be translated along an apex 140 of jaw member 120 such that knife body 130 is slightly flexed thus maintaining a large radius, which, in turn, results to less friction along the wall of knife channel 121. In this manner, knife blade 132 cams along knife channels 111, 113, and 123 of electrode plate 122 while at the same time recessed portion 134 cams along knife channel 121 of jaw member 120. Further, if knife body 130 is urged in an upward direction (e.g. during actuation of knife body 130), bottom portion 122b of electrode plate 122 contains and/or captures recessed portion 134 to thereby prevent knife body 130 from dislodging from knife channel 121. This novel configuration prevents knife splaying which may result to unsuccessful tissue treatment.

Figure 6:
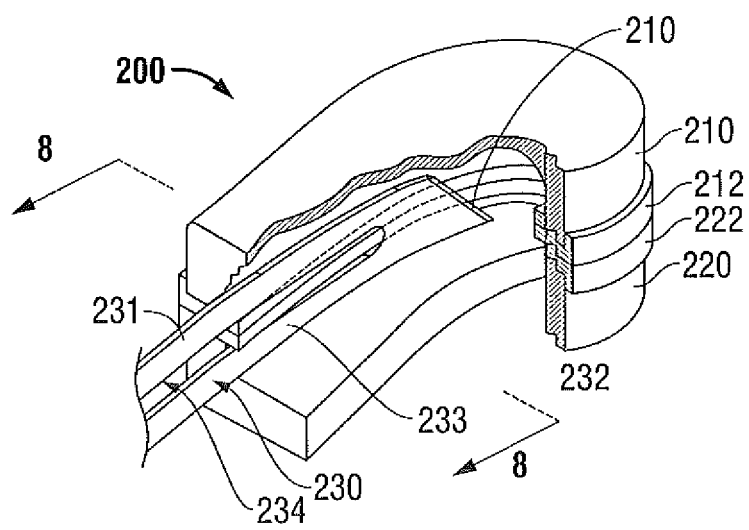
FIG. 6 is a rear, cut-out, perspective view of a jaw member of an end effector assembly showing a knife body actuated therethrough, according to another embodiment of the present disclosure.
Figure 7:
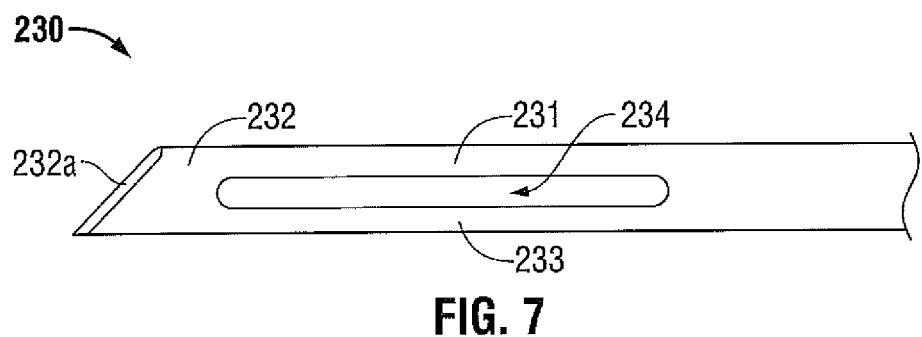
FIG. 7 is a side, elevational view of the knife body of FIG. 6.
Figure 8:
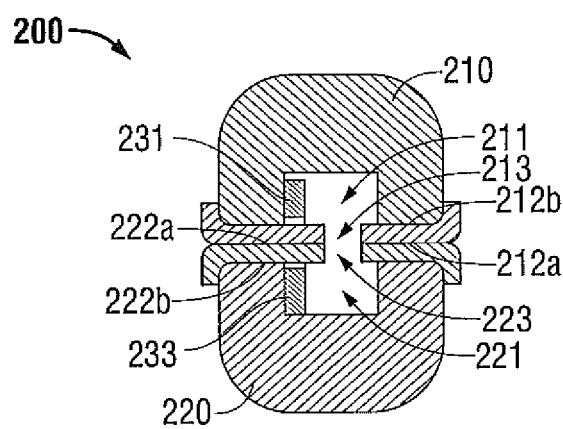
FIG. 8 is a front, cross-sectional view of the end effector assembly of FIG. 6.

Referring now to FIGS. 6-8, another embodiment of end effector assembly 100 will be described and generally depicted as end effector assembly 200. End effector assembly 200 includes a pair of opposing jaw members 210 and 220, each defining a knife channel 211 and 221 therethrough, respectively. Knife channels 211 and 221 are configured to facilitate reciprocation of knife body 230 therethrough when knife body 230 is selectively actuated by a user in order to sever tissue grasped between jaw members 210 and 220. Jaw members 210 and 220 each include an electrode plate 212, 222, respectively, that is disposed atop the jaw members 210 and 220. Each electrode plate 212, 222 includes a top portion 212a and 222a (e.g., tissue contacting surface), respectively, and a bottom portion 212b, 222b, respectively.

In the embodiment shown, top portion 212a, 222a of electrode plate 212, 222 is configured to contact tissue when jaw members 210 and 220 are approximated towards each other in a closed position. The top portion 212a, 222a may also provide the primary energy and surface area for treating tissue (e.g., sealing and coagulation). Each electrode plate 212 and 222 defines a channel 213, 223 to allow access for a knife blade 232 of knife body 230 to pass therethrough. Knife channels 211 and 221 and knife channels 213 and 223 are configured to span along the jaw members 210 and 220 in either a straight configuration or a curved configuration, depending on the configuration of the jaw members 210 and 220.

Knife body 230 includes a knife blade 232 that is positioned on a distal end of knife body 230. A sharp cutting edge is be defined on a distal portion 232a of knife blade 232. In this manner, when the knife blade 232 is translated or reciprocated in a distal direction, distal portion 232a of knife blade 232 may cut and dissect tissue that is grasped between jaw members 210 and 220. Knife body 230 includes a slot portion 234 defined therein that spans along a portion of knife body 230. In this configuration, knife body 230 includes a top portion 231 that is disposed above slot 234 and a bottom portion 233 that is disposed below slot 234.

During use, and typically with a curved jaw configuration, when jaw members 210 and 220 are in the closed, second position and have grasped tissue therebetween, knife trigger assembly 30 is actuated by a user to cause knife body 230 to translate in a distal direction along jaw members 210 and 220. Accordingly, top portion 231 and bottom portion 233, respectively, cam bottom portions 212b, 222b of electrode plates 212, 222. At the same time, knife blade 232 translates in a distal direction through knife channels 213 and 223 to thereby cut tissue disposed between jaw members 210 and 220 along a tissue seal.

In this configuration, slot portion 234 of knife body 230 is guided along bottom portions 212b and 222b of electrode plates 212 and 222 to prevent knife body 230 from splaying. Further, when knife body 230 is in an actuated position, slot portion 234 maintains and captures bottom portions 212b and 222h of electrode plates 212 and 222 to prevent jaw members 210 and 220 from opening to a first, open position. Conversely, the bottom portions 212b and 22b prevent the knife body 230 from dislodging from the preferred knife path.

Figure 9:
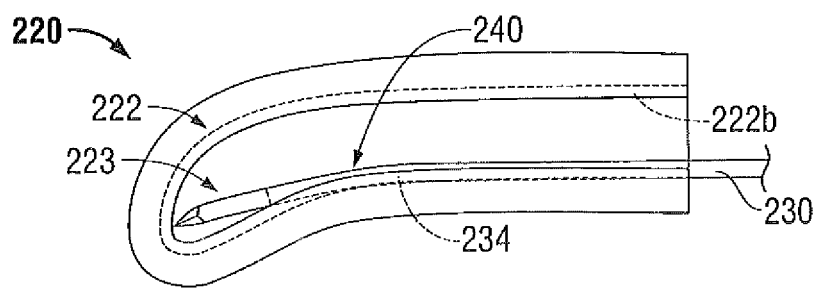
FIG. 9 is a top, plan view of the jaw member and the knife body actuated therethrough, according to an embodiment of the present disclosure.

In some embodiments, and as depicted in FIG. 9, depending on the manufacturing and material of knife body 230, knife body 230 may be translated along an apex 240 of jaw member 220 such that knife body 230 is slightly flexed and maintains a large radius, which, in turn, results to less friction along the wall of knife channel 221. In this manner, knife blade 232 cams along knife channels 213 and 223 of electrode plates 212 and 222, while at the same time top portion 231 and bottom portion 233 captures the inner edges of electrode plates 212 and 222. In addition, an advantage to configuring a blade 240 with slot 234 is that no additional mechanisms are required to prevent jaw members 210 and 220 from opening when the blade 240 is deployed.

Turning now to FIGS. 10-13, another embodiment of end effector assembly 100 will be described and generally depicted as end effector assembly 300. End effector assembly 300 includes jaw members 310 and 320 that are similar to the other jaw members (e.g., 110, 120, 210, and 220) described above, and, as such, only the novel features of end effector assembly 300 will be described. End effector assembly 300 includes a knife body 330 having a proximal portion 330a and a distal portion 330b. Knife body 330 has a tapered configuration such that proximal portion 330a has a width that is larger than a width of distal portion 330b. That is, proximal portion 330a tapers inwardly towards distal portion 330b, as shown in FIGS. 10, 11A and 11B. Knife body 330 includes a knife blade 332 at distal portion 330b. Knife body 330 further includes a slot 334 defined therein that has a top portion 331 and a bottom portion 333.

In use, after the jaw members 310 and 320 are approximated in the closed, second position to grasp tissue therebetween, knife trigger assembly 30 is actuated by a user to cause knife body 330 to translate in a distal direction along jaw members 310 and 320. As knife body 330 is translated in a distal direction, the wider, proximal portion 330a approaches jaw members 310 and 320 such that top portion 331 and bottom portion 333 engage bottom portions 312b and 322b of electrode plates 312 through knife channels 311 and 321. As knife body 330 is distally translated, knife blade 332 of the distal portion 330b moves along knife channels 313 and 323 to thereby cut any tissue that is grasped between jaw members 310 and 320 (e.g., along a tissue seal). In this configuration, the wide proximal portion 330a of tapered knife body 330 captures and maintains jaw members 310 and 320 in a second, closed configuration during a tissue cut. Conversely, the bottom portions 312b and 322b prevent the knife body 330 from dislodging from the preferred knife path.

Figure 12:
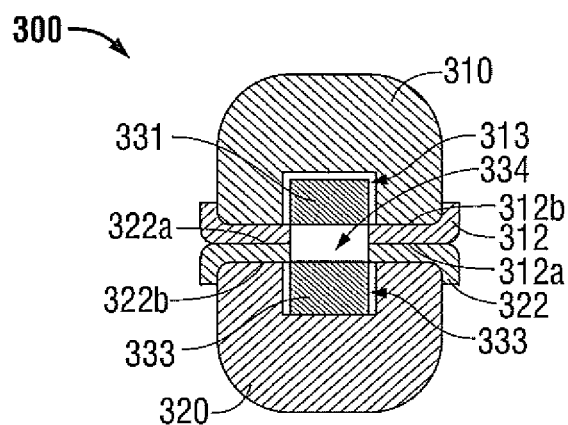
FIG. 12 is a front, cross-sectional view of the end effector assembly taken along the lines 12-12 of FIG. 11B, according to an embodiment of the present disclosure.
Figure 13:
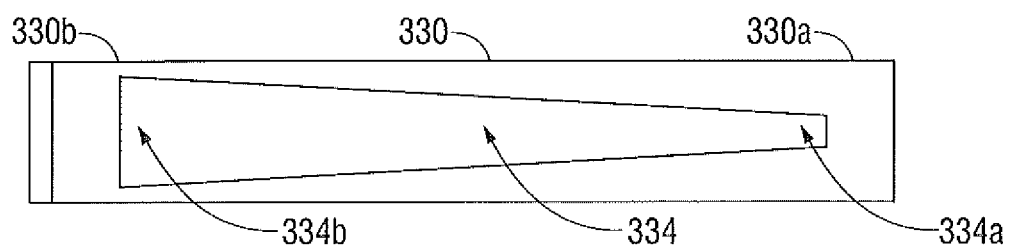
FIG. 13 is a side, elevational view of a knife body of an end effector assembly, according to yet another embodiment of the present disclosure.

In other embodiments, as shown in FIG. 13, slot portion 334 of knife body 330 includes a distal portion 334b that tapers towards a proximal portion 334a such that distal portion 334 has a height that is larger than a height of proximal portion 334a. In this configuration, when jaw members 310 and 320 have tissue grasped therebetween and a tissue cut is necessary, knife body 330 is selectively translated by a user in a distal direction. As knife body 330 is distally translated through knife channels 313 and 323 (as shown in FIG. 12), the tapered slot portion 334 engages bottom surfaces 312b and 322b of the electrode plates 312 and 322 and applies pressure to the jaw members 310 and 320 to apply further pressure to tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly, comprising:
   first and second jaw members defining a centerline, having a curved configuration, and disposed in opposed relation to each other, at least one of the first and second jaw members moveable from a first, open position to a second, closed position for grasping tissue therebetween, at least one of the first and second jaw members including an electrically conductive sealing surface, each of the first and second jaw members including an electrode plate and a ledge, at least one of the ledges disposed along a length of at least one of the first and second jaw members, each ledge including a top portion and a bottom portion;
   at least one of the first and second jaw members including:
      a first knife channel defined along a length of at least a portion of one of the ledges, and
      a second knife channel defined along at least a portion of the length of at least one of the first and second jaw members, and below the bottom portion of a first one of the ledges such that the first one of the ledges covers a portion of the second knife channel; and
   a knife body including a knife blade at a distal end thereof and a recessed portion proximal to the knife blade, wherein the knife blade is configured to travel within the first knife channel and the recessed portion is configured to travel within the second knife channel, wherein as the knife blade and the recessed portion travel within respective first and second knife channels, the knife blade and the recessed portion are positioned to move from a first position aligned with the centerline of the first and second jaw members to a second position laterally offset from the centerline of the first and second jaw members.

2. The end effector assembly according to claim 1, wherein the knife blade is configured to cam along the first knife channel and the recessed portion is configured to cam along the second knife channel under the bottom portion of one of the ledges.

3. The end effector assembly according to claim 1, wherein the knife body is translated along an apex of the first and second jaw members such that the knife body flexes to maintain a radius to reduce friction along a wall of at least one of the first and second knife channels.

4. The end effector assembly according to claim 1, wherein the bottom portion of one of the ledges captures the recessed portion of the knife body to prevent the knife body from dislodging in an upward, distal direction and out of the first knife channel.

5. The end effector assembly according to claim 1, wherein at least one of the first and second jaw members is adapted to connect to an electrosurgical energy source to communicate energy to tissue disposed between the first and second jaw members.

6. The end effector assembly according to claim 1, wherein the top portions of the electrode plates oppose each other and are configured to contact and grasp tissue when the first and second jaw members are approximated towards each other in the closed position.

7. The end effector assembly according to claim 1, wherein a sharp cutting edge is defined on proximal and distal portions of the knife blade such that when the knife blade is translated in a distal direction, the distal portion of the knife blade cuts tissue a first time, and when the knife blade is translated in a proximal direction, the proximal portion of the knife blade cuts tissue a second time.

8. The end effector assembly according to claim 7, wherein each of the sharp cutting edges on the knife blade are disposed at an angle relative to the longitudinal axis of the knife body, the angle being non-perpendicular to, and non-coaxial with, the longitudinal axis of the knife body.

9. An end effector assembly, comprising:
   first and second jaw members defining a centerline, having a curved configuration, and disposed in opposed relation to each other, at least one of the first and second jaw members moveable from a first, open position to a second, closed position for grasping tissue therebetween,
   each of the first and second jaw members including:
      an electrode plate for sealing tissue including a top portion and a bottom portion; and
      a ledge;
   at least one of the first and second jaw members including:
      a first knife channel defined along a length of at least a portion of one of the electrode plates;
      a second knife channel defined along a length of at least a portion of one of the first and second jaw members, the one of the first and second jaw members disposed below the bottom portion of one of the electrode plates; and
   a knife body including a knife blade at a distal end thereof and a slot defined therein, the slot configured to span along at least a portion of a length of the knife body, the knife body including a top portion disposed above the slot, and a bottom portion disposed below the slot, wherein the knife blade is configured to cam along at least one of the first and second knife channels and the slot is configured to receive at least one of the electrode plates, wherein as the knife blade cams along at least one of the first and second knife channels, the knife body is positioned to move from a first position aligned with the centerline of the first and second jaw members to a second position laterally offset from the centerline of the first and second jaw members.

10. The end effector assembly according to claim 9, wherein the knife body is translated along an apex of the first and second jaw members such that the knife body flexes to maintain a radius to reduce friction along a wall of at least one of the first and second knife channels.

11. The end effector assembly according to claim 9, wherein the top portion of the knife body cams below the bottom portion of the electrode plate of the first jaw member, and the bottom portion of the knife body cams below the bottom portion of the electrode plate of the second jaw member.

12. The end effector assembly according to claim 9, wherein the slot is configured to capture a portion of at least one of the electrode plates and the bottom portion of at least one of the electrode plates cams along at least one of the top and bottom portions of the knife body.

13. The end effector assembly according to claim 9, wherein the knife blade translates in a distal direction through the second knife channel to thereby cut tissue disposed between the first and second jaw members.

14. The end effector assembly according to claim 9, wherein the slot captures the bottom surface of at least one of the electrode plates to prevent knife splay and maintain the first and second jaw members in the second, closed position.

15. The end effector assembly according to claim 9, wherein at least one of the first and second jaw members is adapted to connect to an electrosurgical energy source to communicate energy to tissue disposed between the first and second jaw members.

16. An end effector assembly, comprising:
 first and second jaw members disposed in opposed relation to each other, at least one of the first and second jaw members moveable from a first, open position to a second, closed position for grasping tissue therebetween,
 each of the first and second jaw members including:
  an electrode plate for sealing tissue including a top portion and a bottom portion; and
  a ledge;
 at least one of the first and second jaw members including:
  a first knife channel defined along a length of at least a portion of one of the electrode plates;
  a second knife channel defined along a length of at least a portion of one of the first and second jaw members, the one of the first and second jaw members disposed below the bottom portion of one of the electrode plates; and
  a knife body including a knife blade at a distal end thereof and a slot defined therein that is proximal to the knife blade, the slot configured to span along at least a portion of a length of the knife body, the knife body including a top portion disposed above the slot, and a bottom portion disposed below the slot, wherein the knife body includes a proximal portion and a distal portion, the knife body having a tapered configuration such that a width of the proximal portion is larger than a width of the distal portion.

17. The end effector assembly according to claim 16, wherein the proximal portion of the knife body cams the bottom portion of one of the electrode plates as the knife body is translated in a distal direction and maintains the first and second jaw members in the second, closed position.

18. The end effector assembly according to claim 16, wherein the slot of the knife body includes a distal portion that tapers towards a proximal portion such that as the knife body is translated in a distal direction, the slot exerts pressure towards inner edges of the electrode plates.

19. The end effector assembly according to claim 16, wherein at least one of the first and second jaw members is adapted to connect to an electrosurgical energy source to communicate energy to tissue disposed between the first and second jaw members.

* * * * *